United States Patent
Caples et al.

(10) Patent No.: US 8,808,273 B2
(45) Date of Patent: Aug. 19, 2014

(54) ELECTROPHYSIOLOGY CATHETER WITH MECHANICAL USE LIMITER

(75) Inventors: Dennis C. Caples, Placentia, CA (US); Keshava Datta, Chino Hills, CA (US)

(73) Assignee: Biosense Webster (Israel) Ltd. (IL)

( * ) Notice: Subject to any disclaimer, the term of this patent is extended or adjusted under 35 U.S.C. 154(b) by 156 days.

(21) Appl. No.: 13/370,607

(22) Filed: Feb. 10, 2012

(65) Prior Publication Data

US 2013/0211399 A1    Aug. 15, 2013

(51) Int. Cl.
  *A61M 25/00*  (2006.01)
  *A61B 1/00*  (2006.01)
  *A61M 25/18*  (2006.01)

(52) U.S. Cl.
  USPC ............ 604/528; 600/106; 600/125; 604/536

(58) Field of Classification Search
  CPC ................ A61B 18/1492; A61B 2017/00022; A61M 25/0136
  USPC ............................ 600/106, 125; 604/528, 536
  See application file for complete search history.

(56) References Cited

U.S. PATENT DOCUMENTS

| 5,053,015 | A | * | 10/1991 | Gross ........................ 604/167.02 |
| 5,383,374 | A |   | 1/1995  | Reynolds |
| 5,391,199 | A |   | 2/1995  | Ben-Haim |
| 5,989,240 | A |   | 11/1999 | Strowe |
| 6,239,724 | B1 |  | 5/2001  | Doron et al. |
| 6,332,089 | B1 |  | 12/2001 | Acker et al. |
| 6,394,983 | B1 |  | 5/2002  | Mayoral et al. |
| 6,484,118 | B1 |  | 11/2002 | Govari |
| 6,618,612 | B1 |  | 9/2003  | Acker et al. |
| 6,690,963 | B2 |  | 2/2004  | Ben-Haim et al. |
| 2001/0029337 | A1 | * | 10/2001 | Pantages et al. ............... 600/463 |
| 2002/0065455 | A1 |  | 5/2002  | Ben-Haim et al. |
| 2003/0120150 | A1 |  | 6/2003  | Govari |
| 2004/0068178 | A1 |  | 4/2004  | Govari |
| 2006/0025651 | A1 |  | 2/2006  | Adler et al. |
| 2006/0025751 | A1 |  | 2/2006  | Roy et al. |

FOREIGN PATENT DOCUMENTS

WO    WO 96/05768 A1    2/1996

* cited by examiner

*Primary Examiner* — Linda Dvorak
*Assistant Examiner* — Brian M Antiskay

(57) ABSTRACT

A catheter for the treatment of tissue, particularly for the treatment of cardiac tissue to alleviate cardiac arrhythmias includes a connector having mechanical use limiter that may be placed in the handle of the catheter or at any point along the electrical connection pathway to an electro-anatomic mapping system and/or ablation system. The mechanical use limiter has a counter wheel and locking pin which when engaged disables the reconnection of the connector to any mated connector after a predetermined number of uses.

15 Claims, 4 Drawing Sheets

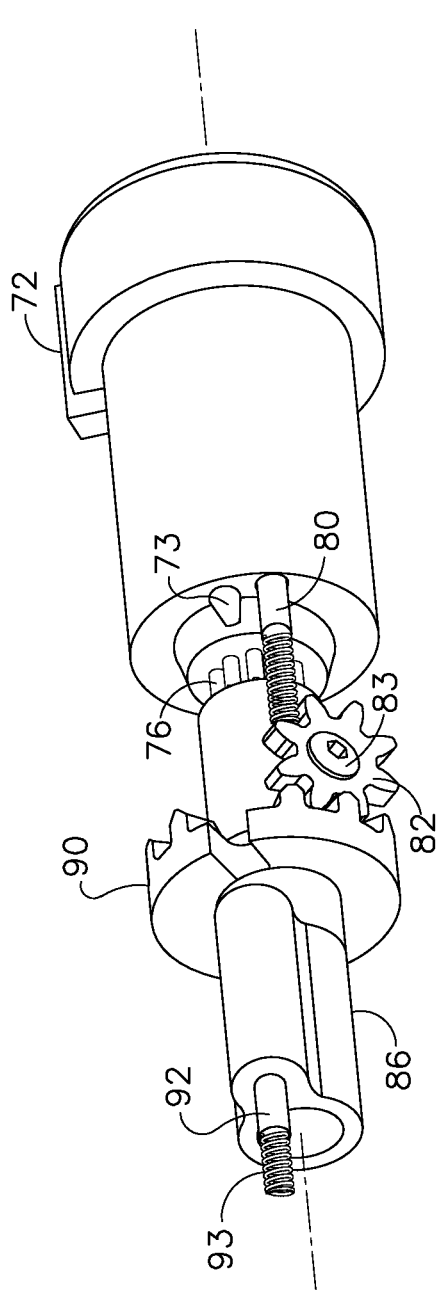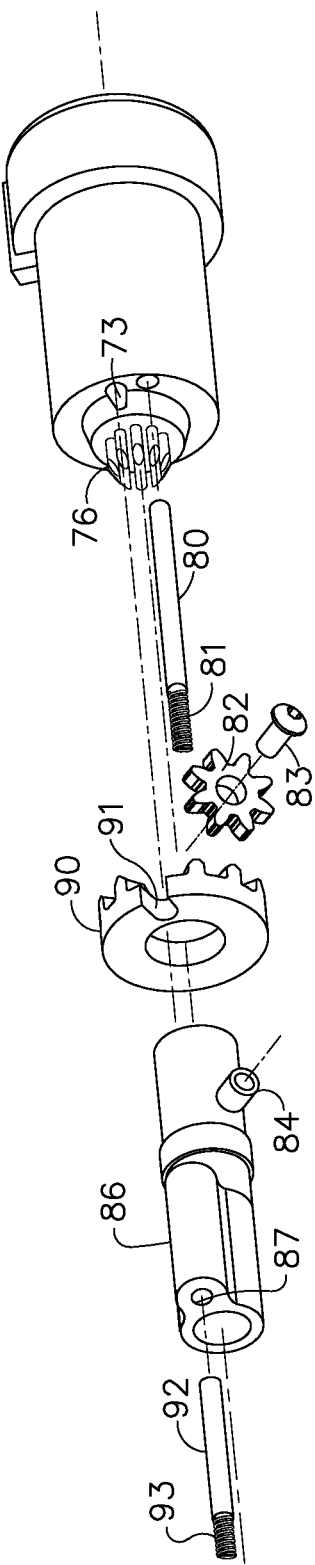
FIG. 3
FIG. 4

ELECTROPHYSIOLOGY CATHETER WITH MECHANICAL USE LIMITER

FIELD OF THE INVENTION

The present invention relates to a catheter for the treatment of human tissue, particularly cardiac tissue and more particularly cardiac arrhythmias, including atrial fibrillation. Such electrophysiology catheters have control handles which contain important circuitry related to their use and the connectors which connect the circuitry to electro anatomic mapping systems and/or radio-frequency (RF) generators. The present invention concerns a connector for such a catheter or other similar devices that limits the use or reuse of the catheter or other devices to a predetermined number of uses.

BACKGROUND OF INVENTION

Cardiac arrhythmias, atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self propagating. Alternatively, or in addition to the multiwavelet reentrant type, cardiac arrhythmias may also have a focal origin, such as when an isolated region of tissue in an atrium fires autonomously in a rapid, repetitive fashion. Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

One type of arrhythmia, atrial fibrillation, occurs when the normal electrical impulses generated by the sinoatrial node are overwhelmed by disorganized electrical impulses that originate in the atria and pulmonary veins causing irregular impulses to be conducted to the ventricles. An irregular heartbeat results and may last from minutes to weeks, or even years. Atrial fibrillation (AF) is often a chronic condition that leads to a small increase in the risk of death often due to strokes. Risk increases with age. Approximately 8% of people over 80 having some amount of AF. Atrial fibrillation is often asymptomatic and is not in itself generally life-threatening, but it may result in palpatations, weakness, fainting, chest pain and congestive heart failure. Stroke risk increases during AF because blood may pool and form clots in the poorly contracting atria and the left atrial appendage. The first line of treatment for AF is medication that either slows the heart rate or revert the heart rhythm back to normal. Additionally, persons with AF are often given anticoagulants to protect them from the risk of stroke. The use of such anticoagulants comes with its own risk of internal bleeding. In some patients, medication is not sufficient and their AF is deemed to be drug-refractory, i.e., untreatable with standard pharmacological interventions. Synchronized electrical cardioversion may also be used to convert AF to a normal heart rhythm. Alternatively, AF patients are treated by catheter ablation. Such ablation is not successful in all patients, however. Thus, there is a need to have an alternative treatment for such patients. Surgical ablation is one option but also has additional risks traditionally associated with surgery.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure—mapping followed by ablation—electrical activity at points within the heart is typically sensed and measured by advancing a catheter containing one or more electrical sensors (or electrodes) into the heart, and acquiring data at a multiplicity of points. These data are then utilized to select the endocardial target areas at which ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical ablation procedure involves the insertion of a catheter having a tip electrode at its distal end into a heart chamber. A reference electrode is provided, generally taped to the skin of the patient or by means of a second catheter that is positioned in or near the heart. RF (radio frequency) current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

Electrophysiology catheters used in mapping and ablation procedures are often connected to electroanatomic mapping systems such as the Carto 3® system from Biosense Webster, Inc. Electroanatomic mapping systems are used in conjunction with mapping catheters to determine the anatomy of the endocardial tissue in the heart and where nerve fibers, nodes and bundles appear on that tissue which may be ablated to treat the aforementioned cardiac arrhythmias.

The handles of electrophysiology catheters for the mapping and ablation of cardiac tissue contain electronic circuitry which converts signals from the tip or ring electrodes near the distal end of the catheter into digital signals that can be communicated to such electroanatomic mapping systems (such as the Carto 3® system from Biosense Webster) and/or an RF generator/ablation system. An electrical connection between the handle and such systems is necessary. This electrical connection is usually accomplished by a "male/female" pin-socket connector such as a Redel™ type connector or other such connector.

Primarily, these types of catheters are sold as single use only devices due to concerns with the ability to properly clean and sterilize the devices for reuse in addition to concerns that certain location sensors or other electronic circuitry in the devices may be damaged during reprocessing and make such devices less reliable in subsequent reuses. Thus, there have been various patents issued concerning the use of electrical counters, etc that can control the use and reuse of such catheters. For example, U.S. Pat. No. 5,383,374 discusses the use of an catheter identification system that generates a signal related to the use or reuse of the catheter. Such systems are complicated to implement.

U.S. patent application Ser. No. 2006/0025651 relates to a connector assembly for the transfer of fluids having a first connector element pertaining to a reservoir and a second connector element pertaining to a medical dosage device which cooperate to give an irreversible connection between the two elements. The first and second elements cooperate with each other by clipping on a single translational movement of a connector element relative to the other to produce the irreversible connection so that at least one of the connection elements has elements to render the same breakable.

U.S. Pat. No. 6,394,983 to Mayoral discloses a cap and luer connector arrangement in which the luer connector sealing lip and seal region are distorted when the sealing lip is received into the crevice during initial screwed-on installation of the cap to the luer connector, forming an external seal. The sealing lip and seal region are heat set during autoclave-sterilization of the cap and luer connector arrangement, which prevents reinstallation of the cap once removed.

U.S. Pat. No. 5,989,240 to Strowe discloses an adapter for attaching a fluid handling device to a catheter including a seat to receive the catheter and a cavity distal to the catheter seat. The adapter further includes a retainer, a rotatable collar disposed over the retainer on the proximal end of the body, with an open port therethrough that is substantially aligned with the passageway to allow placement of the catheter into the passageway. The prevention of returning collar to a first position serves to substantially prevent the adapter from again being mounted onto a catheter and actively substantially prevents reuse of the adapter of the invention.

SUMMARY OF THE INVENTION

The present invention is directed to a mechanical use limiter particularly for use with an electrophysiology ablation and/or mapping catheter having a means for prohibiting the connection of the catheter to an electroanatomic mapping system or ablation system after a predetermined number of uses.

The present invention is also directed to a connector for establishing a mechanical and electrical connection between a medical probe and a system wherein the connector is adapted to connect to a mated connector and includes a mechanical limiter comprising a counter pin movably attached within the connector wherein the counter pin moves when the connector is mated to any mated connector. The mechanical limiter also includes a first rotatable gear having a notch rotated each time the counter pin is moved upon mating the connector to any mated connector and a limiter pin which is biased against the rotatable gear until the notch and limiter pin are aligned wherein the limiter pin moves into a locking position in the connector to block reconnection of the connector to any mated connector thereby blocking connection of the probe to the system.

The connector may also include a second rotatable gear that translates the longitudinal displacement of the counter pin into rotation for rotatable movement of the first rotatable gear. The limiter pin may contain barbs that engage upon movement of the limited pin into a locking position to prevent the movement of the limiter pin. The limiter pin may be comprised of a material which prevents physical alteration of the limiter pin. The mechanical use limiter may be housed in a handle of the medical probe or be placed at any point along the electrical connection between the probe and the system.

The mechanical use limiter may be used in an electrophysiology catheter having a handle and at least one electrode for use with an electrophysiology mapping and ablation system. The connector for connecting the catheter to the system is designed to mate with a mated connector in communication with the system and includes a mechanical limiter capable of blocking reconnection of the connector to any mated connector portion thereby blocking connection of the catheter to the system after a predetermined number of uses.

BRIEF DESCRIPTION OF THE DRAWINGS

These and other features and advantages of the present invention will be better understood by reference to the following detailed description when considered in conjunction with the accompanying drawings wherein:

FIG. 3 is a perspective view of the elements of a mechanical limiter in accordance with the present invention.

FIG. 4 is an exploded perspective view of the elements of a mechanical limiter in accordance with the present invention.

DETAILED DESCRIPTION OF THE INVENTION

Figure 1:
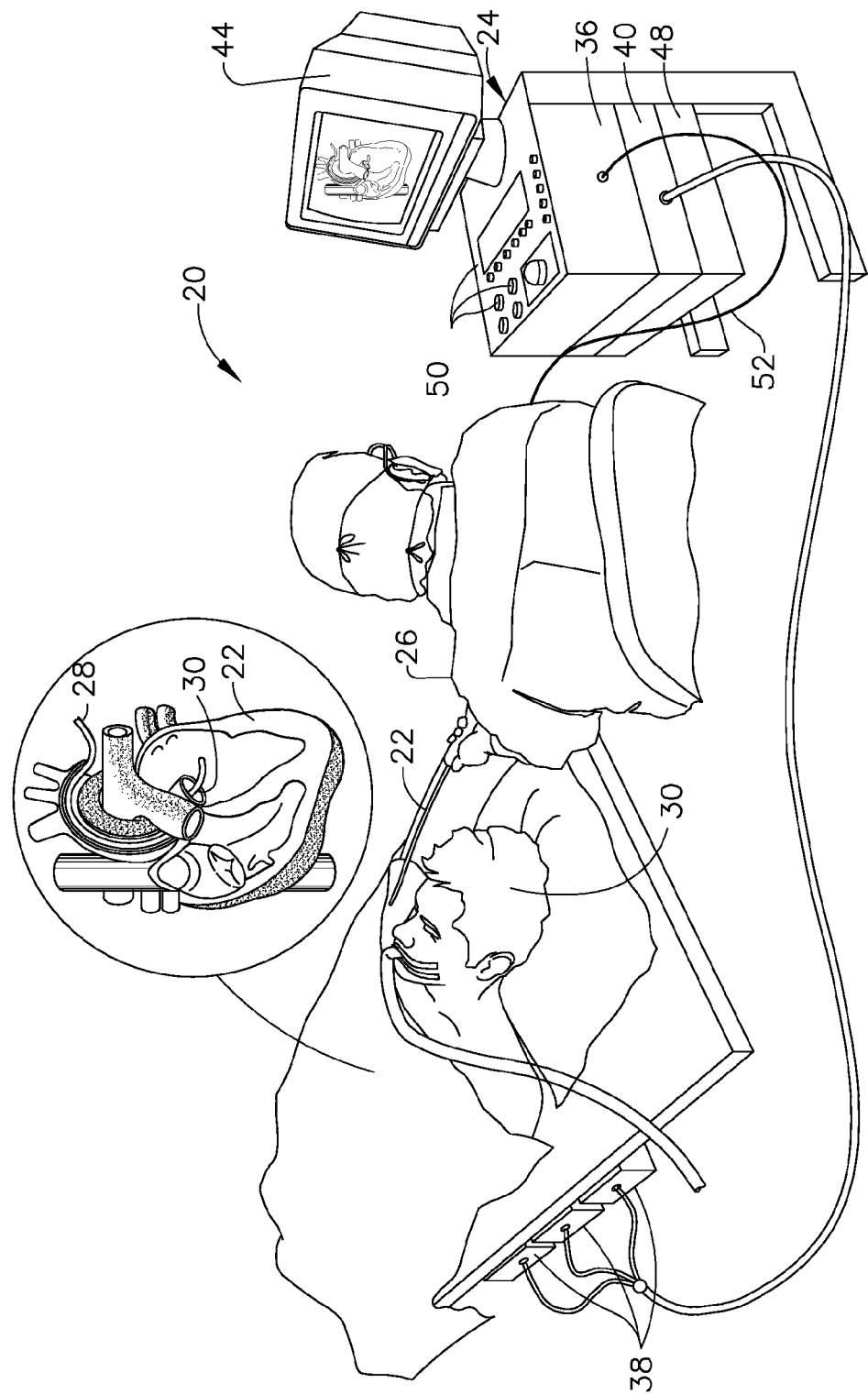
FIG. 1 is a schematic, pictorial illustration of an electrophysiology system for use with a catheter having a mechanical limiter in accordance with an embodiment of the present invention.

Many diagnostic and therapeutic procedures, such as cardiac ablation and intracardiac electoanatomic mapping, use a minimally invasive probe, such as a catheter, which has at least one electrode mounted on its distal tip. The electrode is typically operated when the probe is pressed against a body cavity surface, such as the endocardium in the treatment of cardiac arrhythmias. FIG. 1 is an illustration of a medical system 20 that connects with a catheter having a mechanical limiter in accordance with an embodiment of the present invention. System 20, particularly control console 24, may be based, for example, on the Carto™ systems produced by Biosense Webster, Inc. of Diamond Bar, Calif. System 20 comprises a probe 22, such as an EP ablation or mapping catheter, and a control console 24. In the embodiment described herein, it is assumed that probe 22 is used for diagnostic or therapeutic treatment, such as for mapping electrical potentials in a heart 26 or for performing ablation of endocardial or other tissue of heart 26. However, such a probe 22 may have other uses in the heart or other organs or vasculature of a patient.

An operator 28, such as a cardiologist, electrophysiologist or interventional radiologist inserts probe 22 through the vascular system of a patient 30 so that a distal end 32 of probe 22 enters a chamber of heart 26 (or other body cavity or vasculature). Operator 28 advances probe 22 so that the distal tip 34 of probe 22 engages endocardial tissue at a desired location or locations. Probe 22 is typically connected by a suitable connector at its proximal end to console 24.

Console 24 typically uses magnetic location sensing to determine location coordinates of distal end 32 inside heart 26. For this purpose, a driver circuit 36 in console 24 drives magnetic field generators 39 to generate magnetic fields within the body of patient 30. Typically, the field generators 39 comprise coils, which are placed below the patient's torso at known locations external to the patient 30. These coils generate magnetic fields in a predefined working volume that contains heart 26. A magnetic field sensor 62 within distal end 32 of probe 22 (shown in FIG. 2) generates electrical signals in response to these magnetic fields. A signal processor 49 processes these signals in order to determine the location coordinates of the distal end, typically including both location (x,y,z) and orientation (roll, pitch, yaw) coordinates. This method of location sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Signal processor 49 typically comprises a general-purpose computer, with suitable front end and interface circuits for receiving signals from probe 22 and controlling the other components of console 24. The processor 49 may be programmed in software to carry out the functions that are described herein. The software may be downloaded to console 24 in electronic form, over a network, for example, or it may be provided on tangible media, such as optical, magnetic or electronic memory media. Alternatively, some or all of the functions of processor 49 may be carried out by dedicated or programmable digital hardware components. Based on the signals received from the probe 22 and other components of system 20, processor 49 drives a display 44 to give operator 28 visual feedback through image 46 regarding the location of distal end 32 in the patient's body, as well as status information and guidance regarding the procedure that is in progress. Probe 22 is connected to system 20 through a cable 52. Cable 52 contains electrically conductive wires necessary to connect the electrodes and/or magnetic field sensors to system 20. Cable 52 also comprises a connector (usually male) which is mated to a connector 60 (shown in FIGS. 2-4) in the handle of probe 22 for making a mechanical and electrical connection to the probe 22.

Alternatively or additionally, system 20 may comprise an automated mechanism for maneuvering and operating probe 22 within the body of patient 30. Such mechanisms are typically capable of controlling both the longitudinal motion (advance/retract) of the catheter and transverse motion (deflection/steering) of the distal end of the catheter. Some mechanisms of this sort use DC magnetic fields for this purpose, for example. In such embodiments, processor 49 generates a control input for controlling the motion of the catheter based on the signals provided by the magnetic field sensor in the catheter. These signals are indicative of both the location of the distal end of the catheter and of force exerted on the distal end, as explained further hereinbelow.

Processor 49 stores data representing image 46 in a memory 48. In some embodiments, operator 28 can manipulate image 46 using one or more input devices 50. Although FIG. 1 shows a particular system configuration, other system configurations can also be employed to implement embodiments of the present invention, and are this considered to be within the spirit and the scope of this invention. For example, the methods described hereinbelow may be applied using location transducers of the types other than the magnetic field sensor described above, such as impedance based or ultrasonic location sensors. The term "location transducer" as used herein refers to an element mounted on probe 22 which causes console 24 to receive signals indicative of the coordinates of the element. The locations transducer may comprise a receiver on the probe that generates a location signal to the control unit based on the energy received by the transducer or it may comprise a transmitter, emitting energy that is sensed by a receiver external to the probe. Furthermore, the methods described hereinbelow may similarly be applied to therapeutic and diagnostic applications using not only catheters, but also other types of probes in the heart as well as in other organs and vasculature in the human body.

Figure 2:
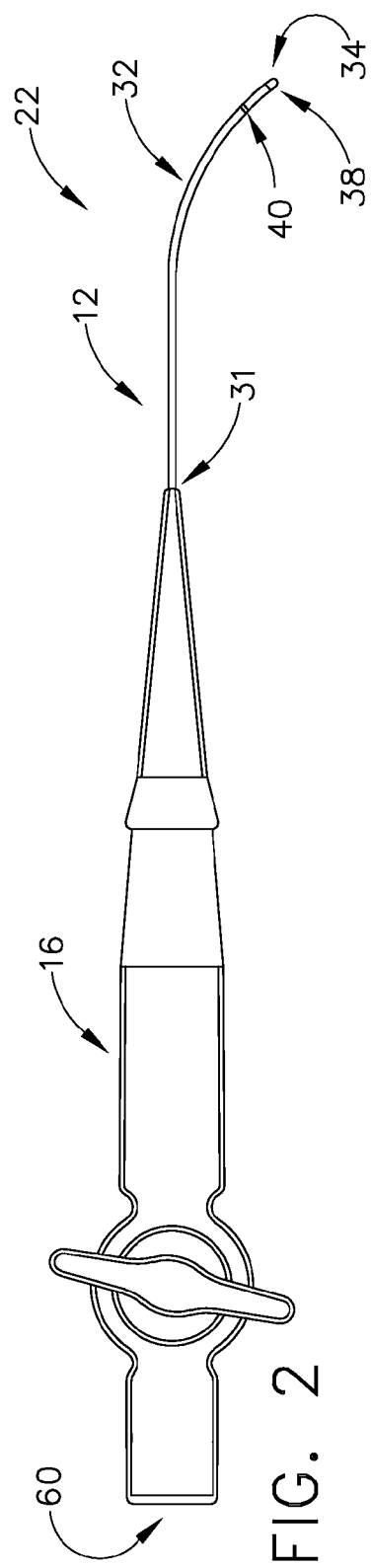
FIG. 2 is an elevational view of an embodiment of a bi-directional electrophysiology catheter having a mechanical limiter in accordance with the present invention.

System 20 may be used with a probe 22 such as steerable bidirectional electrode catheter shown in FIG. 2. In FIG. 2, the catheter or probe 22 comprises an elongated catheter body 12 having proximal end 31 and distal end 32, a tip section 34 with tip electrode 38 at the distal end of the catheter body 12, and a control handle 16 at the proximal end of the catheter body 12. The catheter body 12 comprises an elongated tubular member having a single axial or central lumen (not shown). The catheter body 12 is flexible, i.e., bendable, but substantially non-compressible along its length. The catheter body 12 can be of any suitable construction and made of any suitable material. A presently preferred construction comprises an outer wall made of polyurethane or PEBAX. The outer wall preferably comprises an imbedded braided mesh of stainless steel or the like to increase torsional stiffness of the catheter body 12 so that when the control handle 16 is rotated the tip section 34 will rotate in a corresponding manner.

The overall length and diameter of the probe or catheter 22 may vary according to the application. A presently preferred catheter 22 has an overall length of about 48 inches. The outer diameter of the catheter body 12 is not critical, but is preferably no more than about 8 french. In the depicted embodiment, the distal end of the tip section 14 carries a tip electrode 38. Also mounted along the length of the tip section 34 is a ring electrode 40. The length of the ring electrode 40 is not critical, but is preferably about 1 mm to about 3 mm. Additional ring electrodes can be provided if desired. If multiple ring electrodes are used, they are spaced apart in any fashion as desired so long as their edges do not touch.

The tip electrode 38 and ring electrode 40 are each connected to separate lead wires. Each lead wires (not shown) which extend through a lumen in the distal end 32 through the central lumen in the catheter body 12 and into the control handle 16 where it is connected to electronic circuit board (not shown). Electronic circuit board is connected to an appropriate connector 60, which is adapted to mate to a mated connector on cable 52 so that catheter 22 can be plugged into or otherwise connected to a suitable monitor, source of energy, etc. Alternatively, the lead wires to tip electrode 38 and ring electrode 40 as well as any location sensors in the tip 14 of the catheter 22 may be connected directly to a connector 60 which is then plugged into or otherwise operably connected to a suitable monitor, source of energy etc. The lead wires are connected to the tip electrode 38 and ring electrode 40 by any conventional technique such as solder or the like.

FIGS. 3 and 4 depict the mechanical use limiter of the present invention. A male connector on cable 52 (not shown) preferably having a plurality of pins is used to make an electrical and mechanical contact with the mating female connector 60 in the handle 16 of probe 22. Female connector 60 comprises a housing 72, a plurality of electrical connectors 76 and a counter pin 80 biased by counter spring 81. Electrical connectors 76 are connected to one or more wires (not shown) that are then either connected to the printed circuit board in handle 16 or directly to the electrodes 38 and 40 and location sensors in the tip of the probe. The male connector has at least one pin or prong which is capable of engaging the counter pin 80 thereby causing counter pin 80 to move. After the counter pin 80 is engaged it is pressed against a tooth of first gear 82 which causes first gear 82 to turn counterclockwise thereby translating the longitudinal motion of counter pin 80 into rotational movement. First gear 82 is mounted to mounting tube 86 using mounting screw 83 which engages threads in mount 84 on the side of mounting tube 86. Teeth of first gear 82 engage one or more teeth of second gear 90 which is then rotated around mounting tube 86. Each time the female connector 60 is engaged with a male connector the counter pin is pressed against the first gear 82. Thus, the rotational movement of first gear 82 and second gear 90 can be pre-determined to be equivalent to a certain number of engagements or "uses" of the device being interconnected. Depending on this movement and the starting position of second gear 90 and the location of notch 91 a certain number of "uses" can be pre-determined and mechanically programmed into the limiter.

Figure 5:
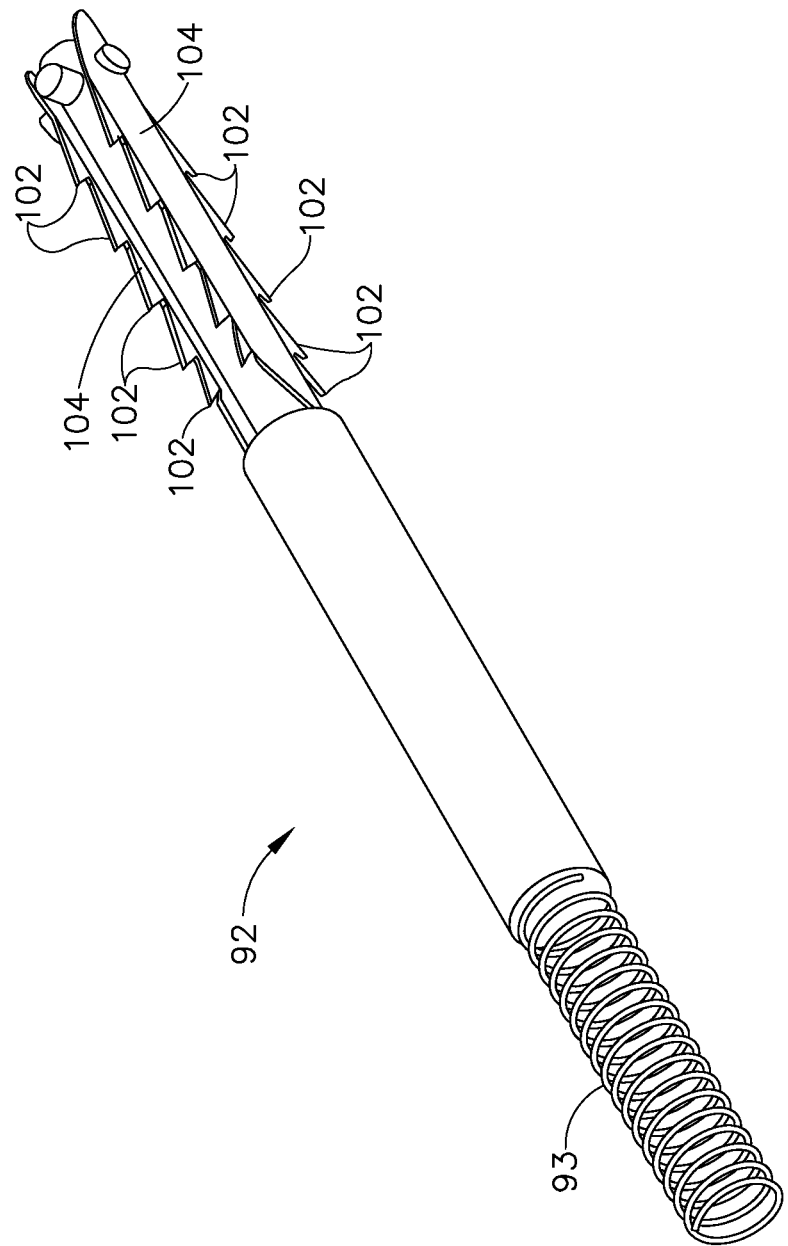
FIG. 5 is a perspective view of the limiter pin for use in a mechanical limiter in accordance with the present invention.

After a successive number of interactions between the male and female connectors, counter pin 80, first gear 82 and second gear 90, notch 91 in second gear 90 is aligned with limiter pin 92. Once notch 91 is aligned with limiter pin 92, limiter pin 92 is "fired" or biased by spring 93 so that limiter pin 92 pushes out of lumen 87 which is coaxial with mounting tube 86 through notch 91 and into lumen 73 in housing 72 of female connector 60. Once male connector on cable 52 is removed, limiter pin 92 prohibits reconnection of the same or another male connector to female connector 60. Barbed or hooked features on the limiter pin 92 prevent manipulation of the limiter pin 92. FIG. 5 shows a perspective view of one possible embodiment of limiter pin 92 having a plurality of barbs 102 along two prongs 104. Limiter pin 92 also may be made of a material that would be difficult to cut or otherwise destroy without destroying the mechanical and electrical connectivity properties of female connector 60 such as stainless steel, titanium, high-carbon stainless steel and the like. Otherwise, the limiter pin 92 and the other components of the mechanical limiter can be made of polycarbonate or other known polymeric materials.

Alternatively, female connector 60 with the mechanical limiter of the present invention could be placed outside of handle 16 connected to handle 16 by a length of wire. Connector 60 does not need to be within handle 16 to have the same connection and use limitation functions.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A connector for establishing a mechanical and electrical connection between a medical probe and a system wherein the connector is adapted to connect to a mated connector and includes a mechanical limiter comprising:

a counter pin movably attached within the connector wherein the counter pin moves when the connector is mated to any mated connector;

a first rotatable gear having a notch rotated each time the counter pin is moved upon mating the connector to any mated connector;

a limiter pin which is biased against the rotatable gear until the notch and limiter pin are aligned wherein the limiter pin moves into a locking position in the connector to block reconnection of the connector to any mated connector thereby blocking connection of the probe to the system.

2. The connector of claim 1 wherein the counter pin is displaced longitudinally when the connector is mated to any mated connector said connector further comprising a second rotatable gear that translates the longitudinal displacement of the counter pin into rotation for rotatable movement of the first rotatable gear.

3. The connector of claim 1 wherein the limiter pin contains barbs that engage upon movement of the limited pin into a locking position to prevent the movement of the limiter pin.

4. The connector of claim 1 wherein the limiter pin is comprised of a material which prevents physical alteration of the limiter pin.

5. The connector of claim 4 where in the material is selected from the group consisting of: stainless steel, high-carbon stainless steel and titanium.

6. The connector of claim 1 wherein mechanical use limiter is housed in a handle of the medical probe.

7. The connector of claim 1 wherein the mechanical use limiter is connected to a handle of the medical probe.

8. The connector of claim 1 wherein the connector is a female connector mated to connect to a male connector.

9. An electrophysiology catheter having a handle and at least one electrode for use with an electrophysiology mapping and ablation system comprising:

a connector for connecting the catheter to the system designed to mate with a mated connector in communication with the system wherein the connector includes a mechanical limiter comprising:

a counter pin movably attached within the connector wherein the counter pin moves when the connector is mated to any mated connector portion;

a first rotatable gear having a notch rotated each time the counter pin is moved upon mating the connector to any mated connector;

a limiter pin which is biased against the rotatable gear until the notch and limiter pin are aligned wherein the limiter pin moves into a locking position in the connector to block reconnection of the connector to any mated connector portion thereby blocking connection of the catheter to the system.

10. The catheter of claim 9 wherein the counter pin is displaced longitudinally when the connector is mated to any mated connector further comprising a second rotatable gear that translates the longitudinal displacement of the counter pin into rotation for rotatable movement of the first rotatable gear.

11. The catheter of claim 9 wherein the limiter pin contains barbs that engage upon movement of the limited pin into a locking position to prevent the movement of the limiter pin.

12. The catheter of claim 9 wherein the limiter pin is comprised of a material which prevents physical alteration of the limiter pin.

13. The catheter of claim 9 where in the material is selected from the group consisting of: stainless steel, high-carbon stainless steel and titanium.

14. The catheter of claim 9 wherein mechanical use limiter resides in the handle of the medical device.

15. The catheter of claim 9 wherein the mechanical use limiter is connected to the handle of the medical device.

* * * * *